US012765943B2

(12) United States Patent
Taff et al.

(10) Patent No.: US 12,765,943 B2
(45) Date of Patent: Oct. 20, 2026

(54) MULTI-LUMEN THROMBECTOMY DEVICES

(71) Applicant: MAGNETO THROMBECTOMY SOLUTIONS LTD., Or Yehuda (IL)

(72) Inventors: Yuval Taff, Tel Aviv (IL); Gal Stern, Tel Aviv (IL); Assaf Torjman, Herzliya (IL)

(73) Assignee: Magneto Thrombectomy Solutions LTD, Or Yehuda (IL)

(*) Notice: Subject to any disclaimer, the term of this patent is extended or adjusted under 35 U.S.C. 154(b) by 712 days.

(21) Appl. No.: 17/418,863

(22) PCT Filed: Feb. 20, 2020

(86) PCT No.: PCT/IB2020/051418
§ 371 (c)(1),
(2) Date: Jun. 28, 2021

(87) PCT Pub. No.: WO2020/174326
PCT Pub. Date: Sep. 3, 2020

(65) Prior Publication Data

US 2022/0071697 A1 Mar. 10, 2022

Related U.S. Application Data

(60) Provisional application No. 62/809,788, filed on Feb. 25, 2019.

(51) Int. Cl.
*A61B 18/14* (2006.01)
*A61B 18/00* (2006.01)

(52) U.S. Cl.
CPC .. *A61B 18/1492* (2013.01); *A61B 2018/0041* (2013.01); *A61B 2018/1435* (2013.01)

(58) Field of Classification Search
CPC ........ A61B 18/1492; A61B 2018/0041; A61B 2018/1435; A61B 2018/1437; A61B 17/22; A61B 2218/007
See application file for complete search history.

(56) References Cited

U.S. PATENT DOCUMENTS 4,027,674 A 6/1977 Tessler et al.
4,682,596 A 7/1987 Bales et al.
(Continued)

FOREIGN PATENT DOCUMENTS

CN 103732169 A 4/2014
CN 104207844 A 12/2014
(Continued)

OTHER PUBLICATIONS

U.S. Appl. No. 15/859,776 Office Action dated Oct. 18, 2021.
(Continued)

*Primary Examiner* — Joanne M Rodden
*Assistant Examiner* — Davina E. Lee

(57) ABSTRACT

An apparatus (20) for treating a blockage in a body of a subject includes a tube (22) configured for insertion into the body and shaped to define: a first lumen (24), and a second lumen (26) having a distal opening (28). The apparatus further includes a pair of electrodes configured to apply an electric current to the blockage upon application of a voltage between the electrodes, the pair including an outer electrode (30) wrapped around the tube and an inner electrode (32) configured to pass through the first lumen. Other embodiments are also described.

27 Claims, 5 Drawing Sheets

(56) References Cited

U.S. PATENT DOCUMENTS

| | | | | |
|---|---|---|---|---|
| 5,122,136 | A | 6/1992 | Guglielmi et al. | |
| 5,125,928 | A | 6/1992 | Parins et al. | |
| 5,300,068 | A | 4/1994 | Rosar et al. | |
| 5,354,295 | A | 10/1994 | Guglielimi et al. | |
| 5,433,708 | A | 7/1995 | Nichols et al. | |
| 5,449,357 | A | 9/1995 | Zinnanti | |
| 5,507,743 | A | 4/1996 | Edwards et al. | |
| 5,545,193 | A | 8/1996 | Fleischman et al. | |
| 5,569,204 | A | 10/1996 | Cramer | |
| 5,603,731 | A | 2/1997 | Whitney | |
| 5,722,401 | A | 3/1998 | Pietroski et al. | |
| 5,827,278 | A | 10/1998 | Webster | |
| 5,851,206 | A | 12/1998 | Guglielmi et al. | |
| 5,876,398 | A | 3/1999 | Mulier et al. | |
| 5,913,854 | A | 6/1999 | Maguire et al. | |
| 5,925,042 | A | 7/1999 | Gough et al. | |
| 6,047,700 | A | 4/2000 | Eggers et al. | |
| 6,179,824 | B1 | 1/2001 | Eggers et al. | |
| 6,190,381 | B1 | 2/2001 | Olsen et al. | |
| 6,210,404 | B1 | 4/2001 | Shadduck | |
| 6,248,113 | B1 | 6/2001 | Fina | |
| 6,322,559 | B1 | 11/2001 | Daulton et al. | |
| 6,344,041 | B1 | 2/2002 | Kupiecki et al. | |
| 6,397,850 | B1 | 6/2002 | Scheldrup et al. | |
| 6,554,827 | B2 | 4/2003 | Chandrasekaran et al. | |
| 6,658,288 | B1 | 12/2003 | Hayashi | |
| 6,730,104 | B1 | 5/2004 | Sepetka et al. | |
| 6,855,143 | B2 | 2/2005 | Davision et al. | |
| 7,037,290 | B2 | 5/2006 | Gardeski et al. | |
| 8,002,729 | B2 | 8/2011 | Melsheimer et al. | |
| 8,197,478 | B2 | 6/2012 | Hayashi et al. | |
| 8,473,029 | B2 | 6/2013 | Gerhart et al. | |
| 8,579,893 | B2 | 11/2013 | Hoey | |
| 8,747,416 | B2 | 6/2014 | Hakala et al. | |
| 8,814,859 | B2 | 8/2014 | Drasler et al. | |
| 8,968,304 | B2 | 3/2015 | Katou | |
| 9,795,400 | B2 | 10/2017 | Davidson | |
| 10,258,491 | B2 | 4/2019 | Bar et al. | |
| 10,265,515 | B2 | 4/2019 | Davidson | |
| 10,413,408 | B2 | 9/2019 | Krone et al. | |
| 10,434,295 | B2 | 10/2019 | Stigall et al. | |
| 10,499,939 | B2 | 12/2019 | Davidson | |
| 10,709,463 | B2 | 7/2020 | Girdhar et al. | |
| 10,716,610 | B2 | 7/2020 | Yamanishi et al. | |
| 10,758,303 | B2 | 9/2020 | Kiao et al. | |
| 10,874,410 | B2 | 12/2020 | Scarpine et al. | |
| 10,874,411 | B2 | 12/2020 | Nguyen et al. | |
| 10,912,608 | B2 | 2/2021 | Lam et al. | |
| 10,987,117 | B2 | 4/2021 | Girdhar et al. | |
| 11,058,444 | B2 | 7/2021 | Girdhar et al. | |
| 11,090,071 | B2 | 8/2021 | Girdhar et al. | |
| 11,160,571 | B2 | 11/2021 | Nguyen et al. | |
| 11,191,558 | B2 | 12/2021 | Nguyen et al. | |
| 11,317,931 | B2 | 5/2022 | Davidson | |
| 11,395,668 | B2 | 7/2022 | Girdhar et al. | |
| 11,523,838 | B2 | 12/2022 | Nguyen et al. | |
| 11,633,201 | B2 | 4/2023 | Girdhar et al. | |
| 11,666,350 | B2 | 6/2023 | Nguyen et al. | |
| 2001/0001314 | A1 | 5/2001 | Davison et al. | |
| 2002/0058937 | A1 | 5/2002 | Maltese et al. | |
| 2002/0072764 | A1 | 6/2002 | Sepetka et al. | |
| 2002/0133111 | A1 | 9/2002 | Shadduck | |
| 2003/0045870 | A1 | 3/2003 | Madsen | |
| 2003/0050634 | A1 | 3/2003 | Ellman et al. | |
| 2003/0125787 | A1 | 7/2003 | Shcherinsky | |
| 2003/0130571 | A1 | 7/2003 | Lattouf | |
| 2004/0073243 | A1 | 4/2004 | Sepetka et al. | |
| 2004/0082948 | A1 | 4/2004 | Stewart et al. | |
| 2005/0159739 | A1 | 7/2005 | Paul et al. | |
| 2005/0251134 | A1 | 11/2005 | Woloszko et al. | |
| 2006/0058838 | A1 | 3/2006 | Bose et al. | |
| 2006/0089638 | A1 | 4/2006 | Carmel et al. | |
| 2006/0195137 | A1 | 8/2006 | Sepetka et al. | |
| 2006/0224155 | A1 | 10/2006 | Schmaltz | |
| 2007/0027448 | A1 | 2/2007 | Paul et al. | |

| | | | | |
|---|---|---|---|---|
| 2007/0078457 | A1 | 4/2007 | Paul et al. | |
| 2007/0156082 | A1 | 7/2007 | Scherman | |
| 2007/0156130 | A1 | 7/2007 | Thistle | |
| 2007/0255270 | A1 | 11/2007 | Carney | |
| 2008/0161796 | A1 | 7/2008 | Cao et al. | |
| 2008/0161803 | A1 | 7/2008 | Oral et al. | |
| 2008/0161893 | A1 | 7/2008 | Paul et al. | |
| 2008/0262489 | A1 | 10/2008 | Steinke | |
| 2009/0248012 | A1 | 10/2009 | Maor et al. | |
| 2010/0092939 | A1 | 4/2010 | Belous et al. | |
| 2010/0114017 | A1* | 5/2010 | Lenker | A61B 17/221 606/200 |
| 2010/0312223 | A1 | 12/2010 | Kozak et al. | |
| 2011/0022045 | A1 | 1/2011 | Cao et al. | |
| 2011/0144639 | A1 | 6/2011 | Govari | |
| 2011/0218528 | A1 | 9/2011 | Ogata et al. | |
| 2011/0257649 | A1* | 10/2011 | Geistert | A61B 18/1492 606/41 |
| 2011/0288541 | A1 | 11/2011 | Faure | |
| 2011/0301594 | A1* | 12/2011 | Orion | A61B 18/1492 606/41 |
| 2011/0308527 | A1 | 12/2011 | Harrington et al. | |
| 2012/0130169 | A1 | 5/2012 | Mesallum | |
| 2012/0232374 | A1 | 9/2012 | Werneth et al. | |
| 2012/0239022 | A1 | 9/2012 | Wolfe | |
| 2012/0296262 | A1 | 11/2012 | Ogata et al. | |
| 2013/0090644 | A1 | 4/2013 | Williams | |
| 2013/0123872 | A1 | 5/2013 | Bornzin et al. | |
| 2013/0325003 | A1 | 12/2013 | Kapur et al. | |
| 2013/0325041 | A1 | 12/2013 | Annest et al. | |
| 2014/0074113 | A1 | 3/2014 | Hakala et al. | |
| 2014/0155931 | A1 | 6/2014 | Bose et al. | |
| 2014/0276748 | A1 | 9/2014 | Ku et al. | |
| 2014/0276913 | A1 | 9/2014 | Tah et al. | |
| 2014/0277013 | A1* | 9/2014 | Sepetka | A61B 17/3207 606/159 |
| 2014/0309579 | A1 | 10/2014 | Rubinsky et al. | |
| 2014/0364896 | A1 | 12/2014 | Consigny | |
| 2015/0005792 | A1* | 1/2015 | Ahn | A61B 17/221 606/159 |
| 2015/0038963 | A1 | 2/2015 | Panos et al. | |
| 2015/0133990 | A1 | 5/2015 | Davidson | |
| 2015/0305756 | A1 | 10/2015 | Rosenbluth et al. | |
| 2016/0008014 | A1 | 1/2016 | Rosenbluth et al. | |
| 2016/0066989 | A1 | 3/2016 | Davies et al. | |
| 2016/0166266 | A1 | 6/2016 | Nita | |
| 2016/0287276 | A1 | 10/2016 | Cox et al. | |
| 2017/0014272 | A1 | 1/2017 | Ray et al. | |
| 2017/0079672 | A1 | 3/2017 | Quick et al. | |
| 2017/0105745 | A1 | 4/2017 | Rosenbluth et al. | |
| 2017/0112514 | A1 | 4/2017 | Marchand et al. | |
| 2017/0172648 | A1 | 6/2017 | Germain et al. | |
| 2017/0189041 | A1 | 7/2017 | Cox et al. | |
| 2017/0265878 | A1 | 9/2017 | Marchand et al. | |
| 2017/0348049 | A1* | 12/2017 | Vrba | A61B 18/1492 |
| 2018/0092652 | A1 | 4/2018 | Marchand et al. | |
| 2018/0116717 | A1 | 5/2018 | Taff et al. | |
| 2018/0161085 | A1 | 6/2018 | Shin et al. | |
| 2018/0256176 | A1 | 9/2018 | Cattaneo | |
| 2018/0296240 | A1 | 10/2018 | Rosenbluth et al. | |
| 2018/0353194 | A1 | 12/2018 | Shaffer et al. | |
| 2018/0361116 | A1 | 12/2018 | Quick et al. | |
| 2019/0046219 | A1 | 2/2019 | Marchand et al. | |
| 2019/0070401 | A1 | 3/2019 | Merritt et al. | |
| 2019/0142452 | A1 | 5/2019 | Trosper et al. | |
| 2019/0150959 | A1 | 5/2019 | Cox et al. | |
| 2019/0231373 | A1 | 8/2019 | Quick et al. | |
| 2019/0262069 | A1 | 8/2019 | Taff et al. | |
| 2019/0321071 | A1 | 10/2019 | Marchand et al. | |
| 2019/0388111 | A1 | 12/2019 | Nguyen et al. | |
| 2019/0388112 | A1 | 12/2019 | Nguyen et al. | |
| 2020/0170666 | A1 | 6/2020 | Trosper et al. | |
| 2021/0267612 | A1 | 9/2021 | Girdhar et al. | |
| 2021/0353323 | A1 | 11/2021 | Teigen et al. | |
| 2021/0361314 | A1 | 11/2021 | Teigen et al. | |
| 2022/0015798 | A1 | 1/2022 | Marchand et al. | |
| 2022/0022900 | A1 | 1/2022 | Nguyen et al. | |
| 2022/0125455 | A1 | 4/2022 | Girdhar et al. | |
| 2022/0218372 | A1 | 7/2022 | Nguyen et al. | |

(56) References Cited

U.S. PATENT DOCUMENTS

| | | | |
|---|---|---|---|
| 2022/0218373 | A1 | 7/2022 | Davidson |
| 2022/0387051 | A1 | 12/2022 | Girdhar et al. |
| 2023/0064470 | A1 | 3/2023 | Girdhar et al. |
| 2023/0113257 | A1 | 4/2023 | Nguyen et al. |

FOREIGN PATENT DOCUMENTS

| | | | |
|---|---|---|---|
| CN | 104224318 | A | 12/2014 |
| DE | 102010014778 | A1 | 10/2011 |
| EP | 1602338 | A2 | 12/2005 |
| EP | 1980200 | A2 | 10/2008 |
| EP | 2359764 | A1 | 8/2011 |
| JP | H0663060 | A | 3/1994 |
| JP | H1057392 | A | 3/1998 |
| WO | 9426228 | A1 | 11/1994 |
| WO | 9724993 | A1 | 7/1997 |
| WO | 0062851 | A1 | 10/2000 |
| WO | 0124720 | A1 | 4/2001 |
| WO | 2014025397 | A1 | 2/2014 |
| WO | 2014151123 | A1 | 9/2014 |
| WO | 2015074032 | A1 | 5/2015 |
| WO | 2015076864 | A1 | 5/2015 |
| WO | 2018172891 | A1 | 9/2018 |
| WO | 2019102307 | A1 | 5/2019 |
| WO | 2019243992 | A1 | 12/2019 |

OTHER PUBLICATIONS

JP Application # 2019546193 Office Action dated Oct. 26, 2021.
JP Application # 2019531818 Office Action dated Nov. 2, 2021.
CN Application # 2018800054493 Office Action dated Nov. 9, 2021.
U.S. Appl. No. 16/381,014 Office Action dated Dec. 7, 2021.
International Application # PCT/IB2021058330 Search Report dated Jan. 12, 2022.
CN Application # 201880017216.5 Office Action dated Dec. 9, 2021.
CN Application # 2018800172165 Office Action dated Apr. 24, 2022.
JP Application # 2022002663 Office Action dated Mar. 7, 2023.
Gross et al., "Dump the pump: manual aspiration thrombectomy (MAT) with a syringe is technically effective, expeditious, and cost-efficient," Journal of NeuroInterventional Surgery, vol. 10, No. 4, pp. 1-4, year 2017.
EP Application # 18880491.8 Office Action dated Feb. 10, 2022.
U.S. Appl. No. 16/381,014 Office Action dated Feb. 17, 2022.
EP Application # 19823746.3 Search Report dated Mar. 4, 2022.
U.S. Appl. No. 17/052,813 Office Action dated Jan. 11, 2024.
EP Application # 18772459.6 Office Action dated Dec. 13, 2023.
EP Application # 18736539.0 Office Action dated Dec. 14, 2023.
CA Application # 3055267 Office Action dated Oct. 23, 2023.
Sawyer et al., "Electrical Hemostasis in Uncontrollable Bleeding States", Annais of Surgery , vol. 154, Issue 4, pp. 556-562, Oct. 1961.
Gralla et al., "A dedicated animal model for mechanical thrombectomy in acute stroke", American Journal of Neuroradiology, vol. 27, Issue 6, pp. 1357-1361, Jun.-Jul. 2006.
U.S. Appl. No. 15/859,776 Office Action dated Jul. 27, 2021.
U.S. Appl. No. 15/859,776 Office Action dated May 19, 2021.
CN Application # 2018800054493 Office Action dated Jun. 2, 2021.
International Application # PCT/IB2020/051418 Search Report dated Mar. 31, 2020.
EP Application # 18880491.8 Search Report dated Jun. 23, 2021.

* cited by examiner

MULTI-LUMEN THROMBECTOMY DEVICES

CROSS-REFERENCE TO RELATED APPLICATION

The present application claims the benefit of U.S. Provisional Appl. No. 62/809,788, entitled "Multi-lumen thrombectomy device," filed Feb. 25, 2019, whose disclosure is incorporated herein by reference.

FIELD OF THE INVENTION

The present invention relates generally to medical devices and procedures, such as thrombectomy procedures for the removal of thrombi from blood vessels.

BACKGROUND

U.S. Pat. No. 10,028,782 to Orion, whose disclosure is incorporated herein by reference, describes a flexible catheter device capable of being introduced into a body passage and withdrawing fluids therefrom or introducing fluids thereinto. The device includes electrodes configured to apply electrical signals in the body passage for carrying out thrombus dissolution and/or thrombectomy, wherein one of said electrodes is designed to contact the thrombus material and remove it or dissolve it, and wherein the electrical voltage signals are unipolar pulsatile voltage signals.

US Patent Application Publication 2018/0116717 to Taff et al., whose disclosure is incorporated herein by reference, describes an apparatus for removal of a thrombus from a body of a subject. The apparatus includes a first electrode, made of a first conductive metal, a second electrode, made of a second conductive metal that is different from the first conductive metal, and a voltage source, configured to apply a positive unipolar voltage between the first electrode and the second electrode while the first electrode is in contact with the thrombus, and while the second electrode is inside the body of the subject.

US Patent Application Publication 2019/0262069 to Taff et al., whose disclosure is incorporated herein by reference, describes an apparatus that includes an electrically-insulating tube, which includes a distal end having a circumferential wall that is shaped to define one or more perforations, configured for insertion into a body of a subject, an outer electrode, disposed over the distal end of the electrically-insulating tube, and configured to lie at least partly within a thrombus while the electrically-insulating tube is inside the body, and an inner electrode, configured to lie, within the tube, opposite the perforations, while the outer electrode lies at least partly within the thrombus. The outer electrode is configured to attract the thrombus while the outer electrode lies at least partly within the thrombus and the inner electrode lies opposite the perforations, when a positive voltage is applied between the outer electrode and the inner electrode such that electric current flows through the perforations.

International Patent Application Publication WO/2019/102307 to Taff et al., whose disclosure is incorporated herein by reference, describes an apparatus including a tube. The tube is configured to advance to a blockage and includes a proximal hub configured to connect to a suction-applying device such that, following the advancement of the tube to the blockage, a suction force generated by the suction-applying device is applied, via the tube, to the blockage. The apparatus further includes a shaft, including first and second electrically-conductive circumferential portions, configured to pass through the tube. The apparatus further includes first and second electrically-conductive elements, configured to connect the first and second electrically-conductive circumferential portions to respective terminals of a power source. The first electrically-conductive circumferential portion is configured to attract the blockage when a voltage is applied by the power source, via the first and second electrically-conductive elements, between the first and second electrically-conductive circumferential portions, such that the blockage is anchored to the shaft while the suction force is applied to the blockage.

International Patent Application Publication WO/2019/243992 to Taff et al., whose disclosure is incorporated herein by reference, describes an apparatus for removing a blockage from a body of a subject. The apparatus includes a reference electrode, configured for insertion into the body, an electrically-insulative element covering the reference electrode, the electrically-insulative element being shaped to define a gap that exposes a portion of the reference electrode, an active electrode covering the electrically-insulative element, and an electrically-conductive element passing through the reference electrode and electrically connected to the active electrode, the electrically-conductive element being configured to electrically connect the active electrode to a power source such that application, by the power source, of a voltage between the active electrode and the reference electrode causes the active electrode to attract the blockage.

SUMMARY OF THE INVENTION

There is provided, in accordance with some embodiments of the present invention, apparatus for treating a blockage in a body of a subject. The apparatus includes a tube configured for insertion into the body and shaped to define: a first lumen, and a second lumen having a distal opening. The apparatus further includes a pair of electrodes configured to apply an electric current to the blockage upon application of a voltage between the electrodes. The pair includes an outer electrode wrapped around the tube, and an inner electrode configured to pass through the first lumen.

In some embodiments, the tube is further shaped to define at least one other lumen having another distal opening.

In some embodiments, the first lumen and the second lumen are not in fluid communication with one another within the tube.

In some embodiments, the tube is shaped to define one or more apertures beneath the outer electrode.

In some embodiments, the apertures are arranged in a spiral arrangement.

In some embodiments, the tube is shaped to define a lateral access port into the second lumen.

In some embodiments, the lateral access port is slit-shaped.

In some embodiments, the first lumen is distally closed.

In some embodiments, the first lumen and the second lumen run alongside one another.

In some embodiments, the tube includes an internal tubular divider separating the first lumen from the second lumen.

In some embodiments, the tubular divider includes an inwardly-protruding portion of a wall of the tube.

In some embodiments, the apparatus further includes:

an electrically-conductive cap that seals a distal end of the first lumen and contacts the outer electrode; and a wire passing through the first lumen and distally connected to the cap, such that the wire is configured to connect the outer electrode, via the cap, to a power source configured to apply the voltage.

In some embodiments, the wire passes through the inner electrode.

In some embodiments, the cap covers a distal tube-end of the tube and is shaped to define an aperture aligned with the distal opening.

In some embodiments, the second lumen is distal to the first lumen.

In some embodiments, the tube includes:

a proximal tube-portion shaped to define the first lumen; and a distal tube-portion connected distally to the proximal tube-portion and shaped to define the second lumen.

In some embodiments, the outer electrode is wrapped around the proximal tube-portion.

In some embodiments, the distal tube-portion is tapered.

In some embodiments, the proximal tube-portion is further shaped to define at least one other lumen having another distal opening.

In some embodiments, the tube includes an internal wall separating a proximal portion of the tube, which is shaped to define the first lumen, from a distal portion of the tube, which is shaped to define the second lumen.

There is further provided, in accordance with some embodiments of the present invention, a method for treating a blockage in a body of a subject. The method includes inserting a tube into the body, the tube being shaped to define: a first lumen, and a second lumen having a distal opening. The method further includes, subsequently to inserting the tube, applying an electric current to the blockage, by applying a voltage between an outer electrode wrapped around the tube and an inner electrode passing through the first lumen. The method further includes passing at least one item through the distal opening.

In some embodiments, the at least one item includes debris generated by applying the electric current, and passing the debris through the distal opening includes passing the debris through the distal opening by aspirating the debris, through the distal opening, into the second lumen.

In some embodiments, the at least one item includes a guidewire, passing the guidewire through the distal opening includes passing the guidewire through the distal opening prior to inserting the tube, and the method further includes, subsequently to insetting the tube, navigating the tube, over the guidewire, to the blockage.

In some embodiments, the at least one item includes a contrast agent, and passing the contrast agent through the distal opening includes passing the contrast agent, through the distal opening, into blood of the subject.

In some embodiments, the at least one item includes a tool.

In some embodiments, the tool includes a stent, and passing the stent through the distal opening includes passing the stent, through the distal opening, into a conduit in which the blockage is located, such that the stent expands within the conduit.

In some embodiments, the tool includes a net, and the method further includes, subsequently to passing the net through the distal opening, catching fragments of the blockage in the net.

The present invention will be more fully understood from the following detailed description of embodiments thereof, taken together with the drawings, in which;

DETAILED DESCRIPTION OF EMBODIMENTS

Overview

US Patent Application Publication 2019/0262069 to Taff et al., cited above in the Background, describes a thrombectomy device comprising a tube having a distal perforated portion, an outer electrode disposed over the perforated portion, and an inner electrode disposed within the perforated portion. To treat a thrombus within the body of a subject, the outer electrode is lodged within the thrombus, and a positive voltage is then applied between the outer electrode and the inner electrode. As the voltage is applied, an electric current flows through the perforations, causing the thrombus to become electrostatically attracted to the outer electrode. In addition to this electrostatic force, a suction force may be applied to the thrombus via the perforations.

In general, when using the aforementioned device, it is advantageous for the distal end of the tube to be closed, such that the electric current and the suction force may be concentrated at the perforations. However, if the distal end of the tube is closed, it may be difficult or impossible to aspirate debris through the tube or to pass a tool, such as a stent, through the tube into the body.

To address this challenge, embodiments of the present invention provide a multi-lumen tube, which is shaped to define both a closed lumen, which contains the inner electrode, and at least one open lumen. The closed lumen facilitates applying electrostatic and suction forces to the thrombus, while the open lumen facilitates transferring items between the body and the tube. For example, prior to inserting the tube into the subject, a guidewire may be passed through the open lumen, and the tube may then be navigated, over the guidewire, to the thrombus. Alternatively or additionally, to facilitate navigating the tube, a contrast agent may be passed through the open lumen into the subject's body. Alternatively or additionally, a tool for facilitating the treatment may be passed through the open lumen into the subject's body, and/or debris may be aspirated through the open lumen while the voltage is applied.

In some embodiments, the closed lumen and the open lumen run alongside one another within the tube. In other embodiments, the open lumen is distal to the closed lumen.

In alternate embodiments, all the lumens in the tube are distally open. An advantage of such embodiments (as well as of the former embodiments) is that by virtue of the inner electrode being contained within a separate lumen, the inner electrode does not interfere with the passage of debris or tools through the tube.

The devices described herein may be used to treat various types of blockages of bodily conduits. For example, the devices described herein may be used to remove a thrombus or an embolus from a blood vessel, or to remove another type of blockage from a digestive tract.

Apparatus Description

Figure 1:
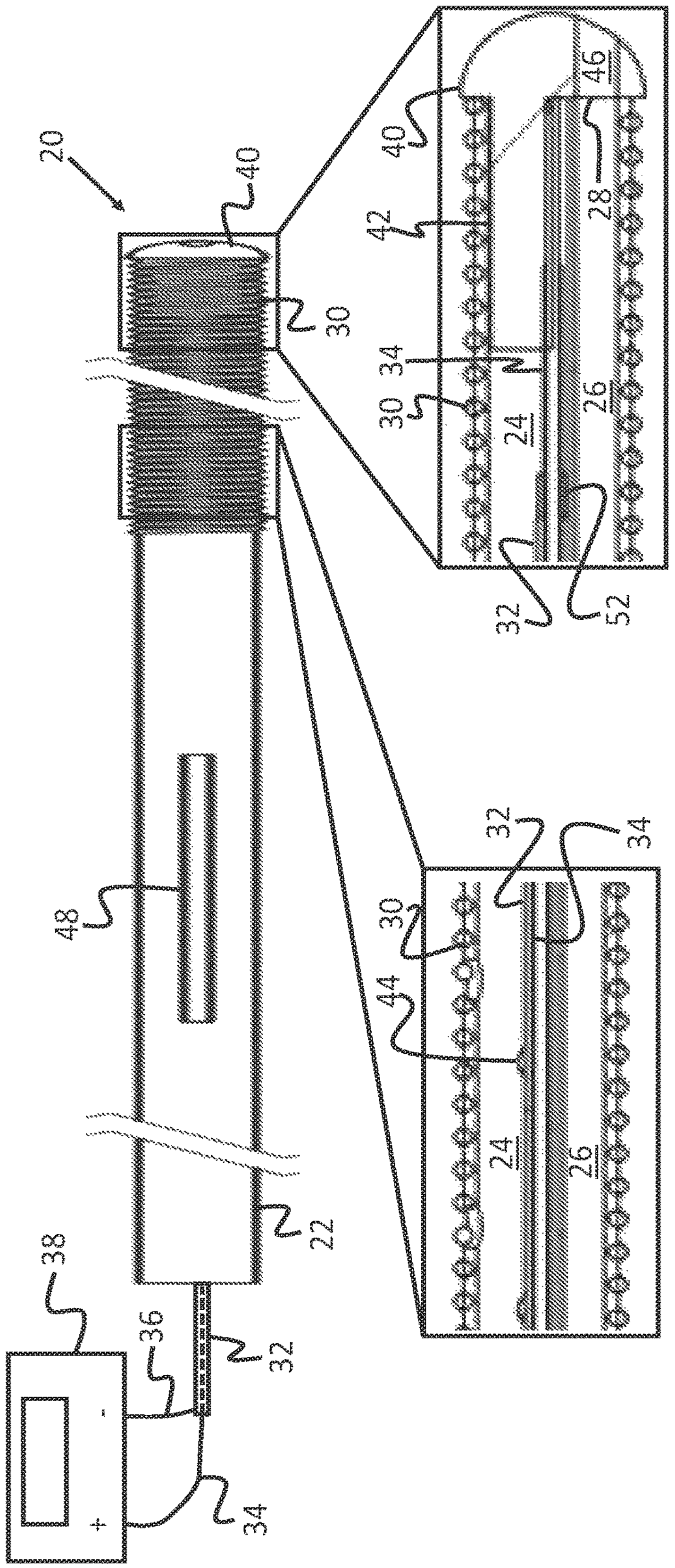
FIG. 1 is a schematic illustration of an apparatus for treating a blockage in a body of a subject, in accordance with some embodiments of the present invention.

Reference is initially made to FIG. 1, which is a schematic illustration of an apparatus 20 for treating a blockage in a body of a subject, in accordance with some embodiments of the present invention. FIG. 1 includes a side view of apparatus 20, along with two longitudinal cross-sections through different respective portions of the apparatus.

Apparatus 20 comprises a multi-lumen tube 22 configured for insertion into the body of the subject. Tube 22 is typically made of a biocompatible polymer such as polyether block amide (PEBA), silicone, polyurethane, polyethylene, and/or polytetrafluoroethene (PTFE). Typically, the length of the tube is between 100 and 200 cm, and/or the outer diameter of the tube is between 1 and 5 mm, such as between 1 and 3 mm.

Tube 22 is shaped to define a first lumen 24, which, typically, is distally closed. For example, apparatus 20 may comprise an end cap 40 that seals the distal end of first lumen 24. Typically, end cap 40 is made of a biocompatible electrically-conductive metal such as stainless steel and/or an alloy of platinum or of gold. In some embodiments, end cap 40 is tapered (i.e., the diameter of the end cap decreases moving distally along the end cap), such that the end cap may pass through the blockage more easily. For example, the end cap may be cone-shaped.

Tube 22 is further shaped to define a second lumen 26 having a distal opening 28. Typically, both first lumen 24 and second lumen 26 run parallel to the longitudinal axis of the tube, i.e., along the length of the tube. Typically, first lumen 24 and second lumen 26 are not in fluid communication with one another within the tube.

In some embodiments, as shown in FIG. 1, the first lumen and the second lumen run alongside one another, each of the lumens typically having a proximal opening at the proximal end of the tube.

Figure 5:
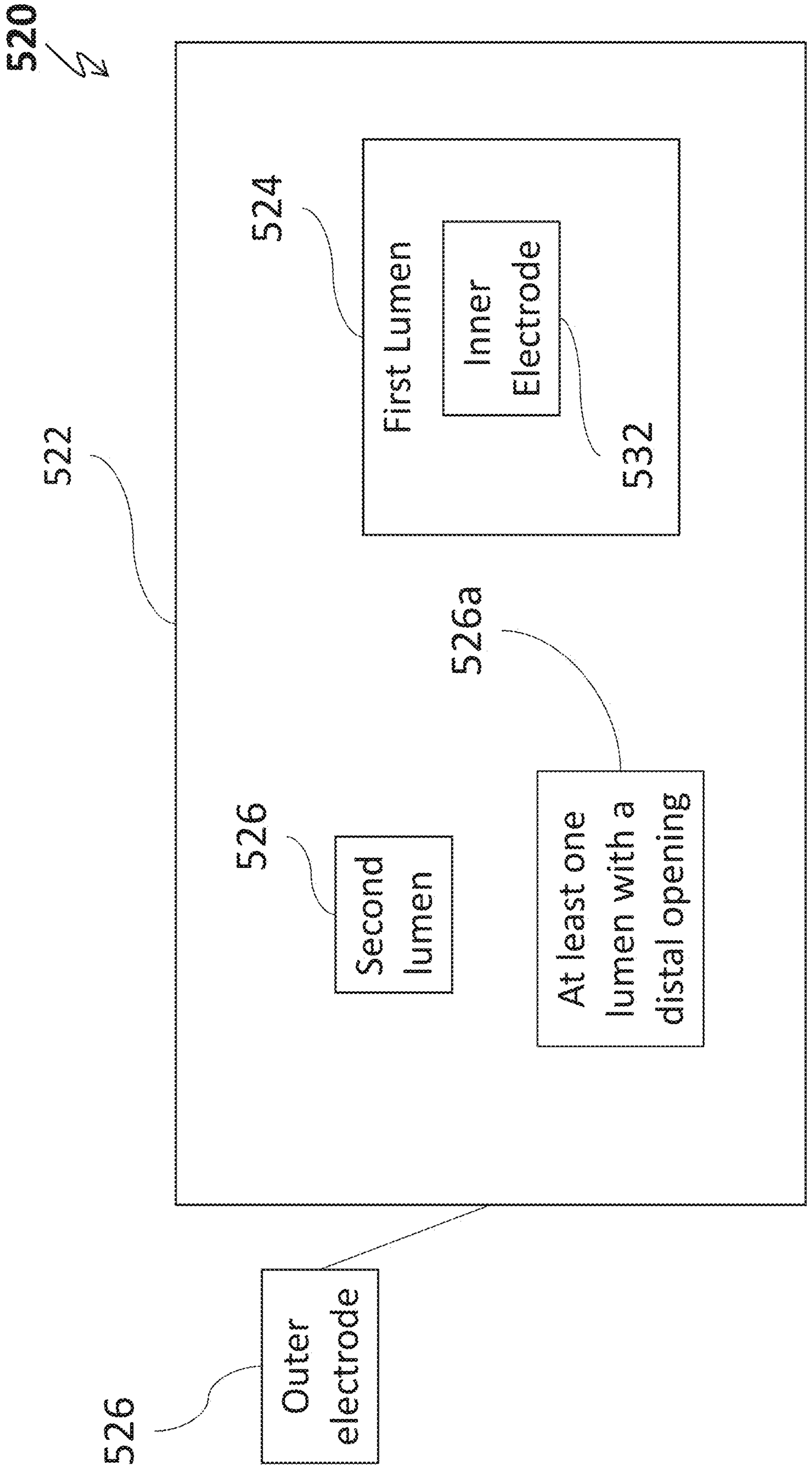
FIG. 5 is a schematic illustration of a block diagram of an apparatus having more than one distally open lumens, in accordance with some respective embodiments of the present invention.

In addition to the first and second lumens, the tube may be shaped to define at least one other lumen (e.g., 526*a*, FIG. 5) having another distal opening. It is to be noted that in FIG. 5, the same reference numerals have been used to denote parts that are the same as or correspond to those of previous embodiments/Figures, having the prefix of 5XX. The inner diameter of each of the lumens in tube 22 is typically at least 0.25 mm, such as at least 0.35 mm Apparatus 20 further comprises a pair of electrodes comprising an outer electrode 30, which is wrapped around the tube, and an inner electrode 32, which is configured to pass through first lumen 24. As further described below, outer electrode 30 and inner electrode 32 are configured to apply an electric current to the blockage upon application of a voltage between the electrodes.

Typically, outer electrode 30 comprises a coil, braid, or mesh. The outer electrode is typically made of a biocompatible electrically-conductive metal such as a gold alloy, a platinum alloy, or another metal plated with gold. Typically, the length of the outer electrode, i.e., the distance between the proximal and distal tips of the outer electrode, is between 10 and 300 mm, e.g., between 30 and 200 mm.

The inner electrode is typically made of a biocompatible electrically-conductive metal such as stainless steel, Nitinol, tungsten, and/or titanium. In some embodiments, the inner electrode is in a fixed position relative to tube 22, e.g., by virtue of the inner electrode being glued and/or otherwise mechanically coupled to tube 22. In other embodiments, the inner electrode is moveable (e.g., axially slidable) within tube 22.

Apparatus 20 further comprises a first wire 34, configured to connect outer electrode 30 to a power source 38. For example, end cap 40 may contact the outer electrode, and first wire 34 may pass through first lumen 24 and distally connect to the end cap, such that, upon the proximal end of the first wire being connected to power source 38, the first wire connects the outer electrode, via the end cap, to the power source. In some such embodiments, end cap 40 comprises a plug 42 that protrudes into, and plugs, first lumen 24, and the first wire is distally connected to plug 42.

In some embodiments, first wire 34 passes through inner electrode 32; for example, the inner electrode may comprise a metallic tube, and the first wire may pass through the lumen of the metallic tube. In other embodiments, the first wire passes through first lumen 24 alongside the inner electrode.

The first wire is typically made of a biocompatible metal such as stainless steel, Nitinol, tungsten and/or titanium, Typically, only the distal end of the first wire, which is connected to the outer electrode (e.g., via end cap 40), is exposed, while the remainder of the first wire is insulated by an insulating layer 52 of a biocompatible material such as a polyimide or silicone. Typically, insulating layer 52 protrudes from inner electrode 32 for at least 1 mm, such as at least 4 ram, at least while the voltage is applied. Thus, the flow of electric current between the more distal exposed portion of first wire 34 and the inner electrode is reduced.

Apparatus 20 further comprises a second wire 36, configured to connect inner electrode 32 to power source 38. Typically, second wire 36 is entirely external to tube 22.

To treat the blockage, the tube is inserted into the body, and is then advanced, typically under fluoroscopy, to the blockage. Typically, the tube is then passed through the blockage such that the outer electrode lies within the blockage. Subsequently, a voltage is applied between the outer electrode and the inner electrode by, using power source 38, applying the voltage between first wire 34 and second wire 36. The application of the voltage between the electrodes causes an electric current to be applied to the blockage.

For example, a positive voltage (e.g., a positive unipolar voltage) may be applied between the outer electrode and the inner electrode, such that the blockage becomes electrostatically attached to the outer electrode. Subsequently, the tube, together with the blockage, may be withdrawn from the body. Alternatively, a negative voltage (e.g., a negative unipolar voltage) may be applied between the outer electrode and the inner electrode, such that the blockage becomes dissolved.

Prior to applying the voltage, while applying the voltage, and/or subsequently to applying the voltage, at least one item may be passed through distal opening 28, either from or into second lumen 26.

For example, prior to inserting the tube, a guidewire may be passed through distal opening 28 (and through the second lumen), Subsequently, the tube may be inserted into the body of the subject and then navigated, over the guidewire, to the blockage. Alternatively or additionally, to facilitate navigating the tube through a blood vessel, a contrast agent may be passed through distal opening 28 into the blood of the subject, e.g., using a syringe or pump disposed at the proximal end of second lumen 26.

Alternatively or additionally, using a suction-applying device, such as a syringe or a pump, disposed at the proximal end of second lumen 26, debris generated by the application of the electric current to the blockage may be aspirated through distal opening 28 into the second lumen. Alternatively or additionally, to facilitate the treatment, a tool may be passed through the distal opening. For example, a stent may be passed, through the distal opening, into the conduit (e.g., the blood vessel) in which the blockage is located, such that the stent expands within the conduit. Alternatively or additionally, a net may be passed through the distal opening, and the net may then be used to catch fragments of the blockage.

Figure 6:
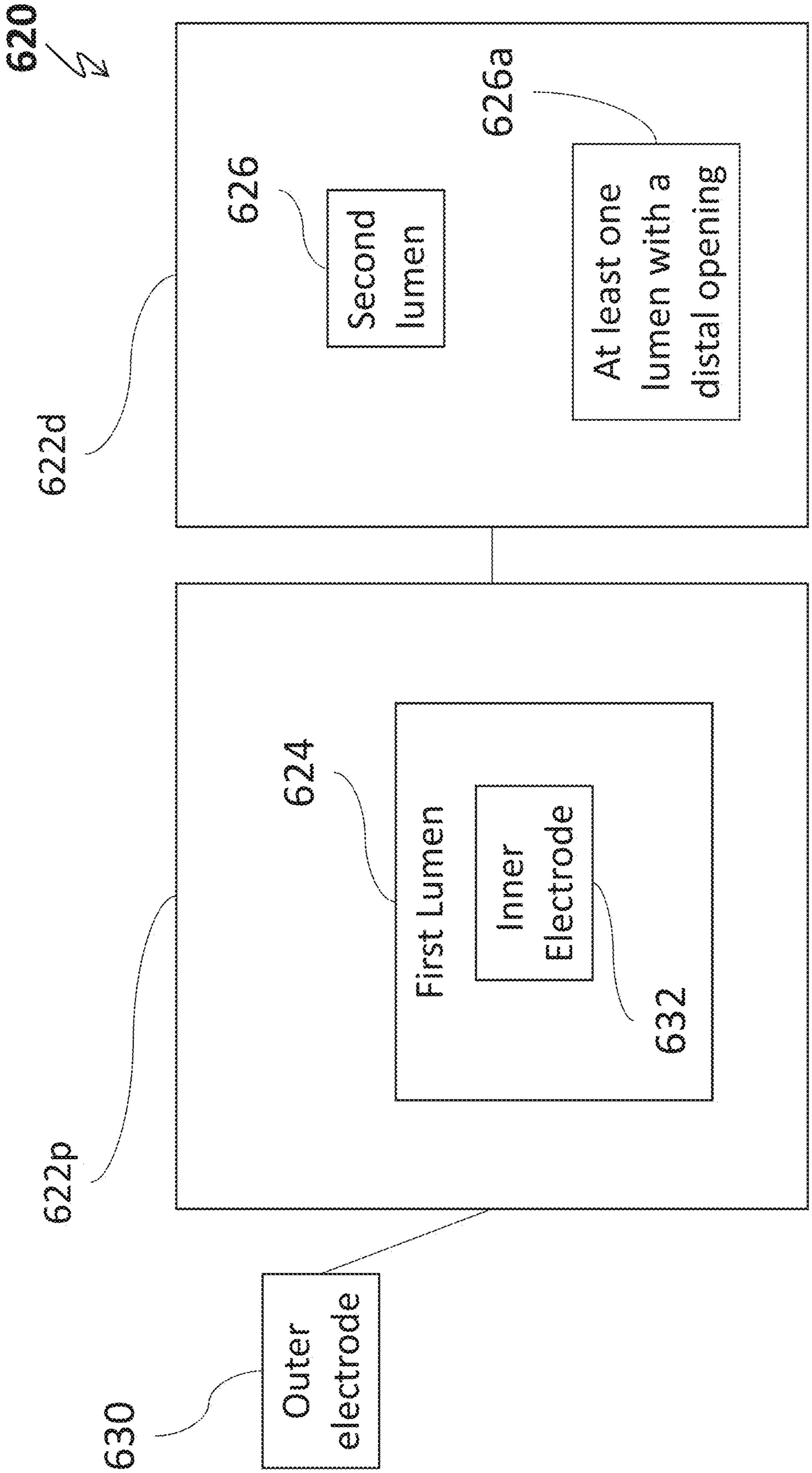
FIG. 6 is a schematic illustration of a block diagram of an apparatus having a proximal tube portion with more than one distally open lumens, in accordance with some respective embodiments of the present invention.

As noted above, tube 22 may be shaped to define multiple distally-open lumens (e.g., 626*a*, FIG. 6). It is to be noted that in FIG. 6, the same reference numerals have been used to denote parts that are the same as or correspond to those of previous embodiments/Figures, having the prefix of 6XX. In such embodiments, the open lumens may perform different respective functions; for example, one lumen may be used for passage of a guidewire, while another lumen may be used for aspiration of debris.

In some embodiments, tube 22 is shaped to define a lateral access port 48 into the second lumen. Lateral access port 48 is typically slit-shaped, in that the length of the port (running parallel to the longitudinal axis of the tube) is greater than the width of the port. Advantageously, this shape facilitates passing a guidewire through the port. Typically, the port is disposed near the distal end of the tube, proximally to (e.g., within 1-100 mm of, such as within 5-50 mm of) the outer electrode. In some embodiments, the length of the port is between 1 and 30 mm, and/or the width of the port is between 0.3 and 3 mm.

In some embodiments, end cap 40 covers the distal end of the tube, and is shaped to define an aperture (or “port”) 46 aligned with distal opening 28. (Similarly, end cap 40 may be shaped to define additional apertures aligned with the respective distal openings of any other distally-open lumens.) In other embodiments, end cap 40 seals first lumen 24 without covering the rest of the distal end of the tube. In yet other embodiments, end cap 40 is shaped to define an aperture aligned with first lumen 24, or apparatus 20 does not comprise end cap 40 at all, such that the first lumen is distally open.

Typically, tube 22 is shaped to define one or more apertures (or “perforations”) 44 beneath the outer electrode, and inner electrode 32 is disposed opposite the apertures, at least while the voltage is applied. Hence, as the voltage is applied between the electrodes, electric current may flow, through the apertures, between the electrodes. (Typically, at least while the voltage is applied, the distance between end cap 40 and inner electrode 32 is greater than 1 mm, such as greater than 4 mm, such that relatively little electric current flows between the end cap and the inner electrode via first lumen 24.) Furthermore, using a suction-applying device, such as a syringe or a pump, at the proximal end of first lumen 24, a suction force may be applied to the blockage via the apertures.

Figure 2:
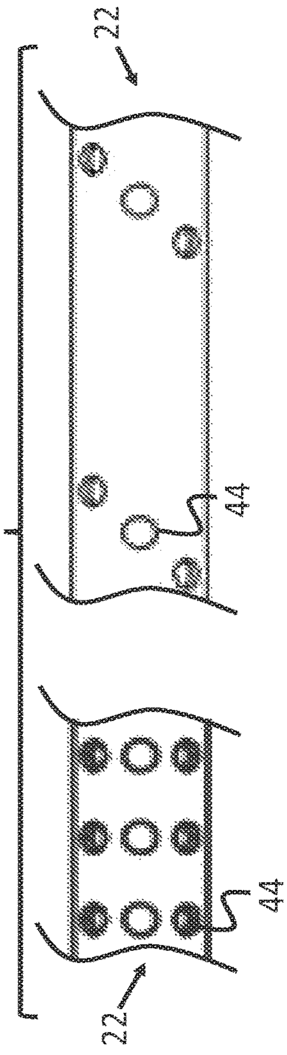
FIG. 2 is a schematic illustration of apertures in a tube, in accordance with some embodiments of the present invention.

For more details concerning apertures 44, reference is now made to FIG. 2, which is a schematic illustration of apertures 44, in accordance with some embodiments of the present invention.

In general, apertures 44 may be arranged in any suitable arrangement. For example, apertures 44 may be arranged in one or more rows running parallel to the longitudinal axis of the tube, as shown at the left of FIG. 2. (Typically, the distance between each pair of adjacent apertures in each row is between 0.5 mm and 5 mm.) Alternatively, for example, apertures 44 may be arranged in a spiral arrangement, as shown at the right of FIG. 2. Advantageously, a spiral arrangement may allow for greater mechanical integrity of the tube, relative to other arrangements.

Typically, the diameter of each aperture 44 is greater than 0.05 mm, such as between 0.1 mm and 2 mm, e.g., between 0.1 mm and 1 mm. Typically, the apertures are distributed throughout the length of outer electrode 30.

Alternatively or additionally to the properties described above, the apertures may have any of the properties described in US Patent Application Publication 2019/0262069 to Taff et al., whose disclosure is incorporated herein by reference. For example, the apertures may have varying diameters, as described with reference to FIGS. 3A-B of the aforementioned application, such that the suction force may be concentrated at the larger apertures. As a specific example, the diameter of one or more apertures near the center of the outer electrode, or near the proximal end of the outer electrode, may be greater than that of the other apertures. Alternatively or additionally, the spacing between successive apertures may vary, such that a greater number of apertures are disposed at the particular portion of the electrode than at other portions of the electrode.

In some embodiments, the sum of the surface areas of the apertures is between 50% and 200%, e.g., between 90% and 110%, of the cross-sectional area of first lumen 24 (FIG. 1). As a purely illustrative example, if the cross-sectional area of the first lumen is 1 $mm^2$ and there are 10 apertures, each aperture may have a surface area of 0.1 $mm^2$, such that the sum of the aperture surface-areas is also 1 $mm^2$. This matching of surface areas may help prevent pressure drops from occurring along the tube.

Figure 3B:
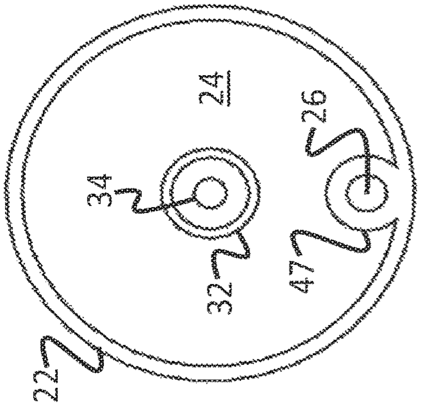
FIGS. 3A-B are schematic illustrations of transverse cross-sections through a tube, in accordance with different respective embodiments of the present invention.
Figure 3A:
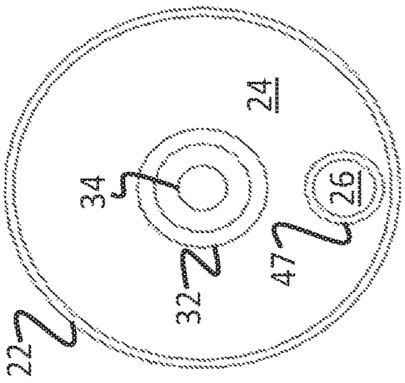

Reference is now made to FIGS. 3A-B, which are schematic illustrations of transverse cross-sections through tube 22, in accordance with different respective embodiments of the present invention.

In some embodiments, as shown in FIGS. 3A-B, tube 22 comprises an internal tubular divider 47 separating the first lumen from the second lumen. (Either the first lumen or the second lumen may be contained within tubular divider 47.) In some such embodiments, as shown in FIG. 3A, tubular divider 47 is not coupled to the lateral watt of the tube, but rather, is coupled to end cap 40 in alignment with aperture 46 (FIG. 1) or is not coupled to the tube at all. In other such embodiments, as shown in FIG. 3B, the tubular divider comprises an inwardly-protruding portion of the wall of the tube. Such a protrusion may be formed, for example, during the manufacture (e.g., extrusion) of the tube.

Figure 4A:
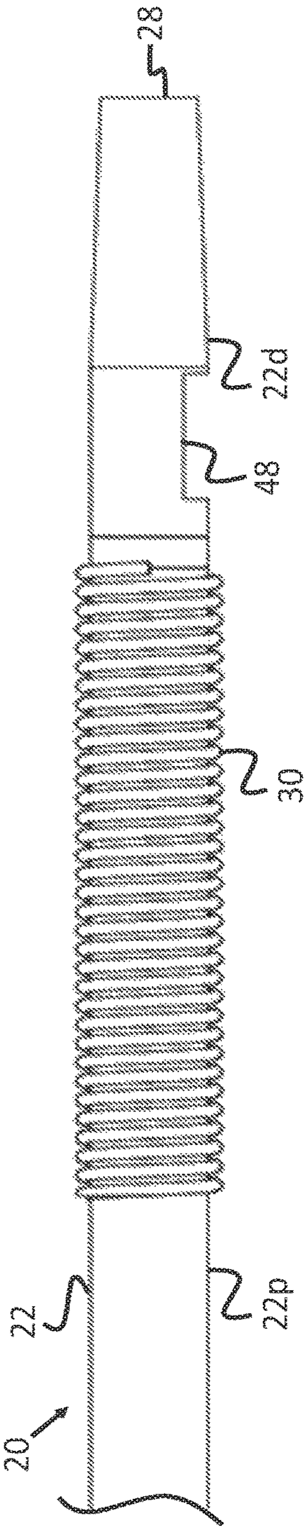
FIG. 4A is a schematic illustration of an apparatus for treating a blockage in a body of a subject, in accordance with other embodiments of the present invention.
Figure 4B:
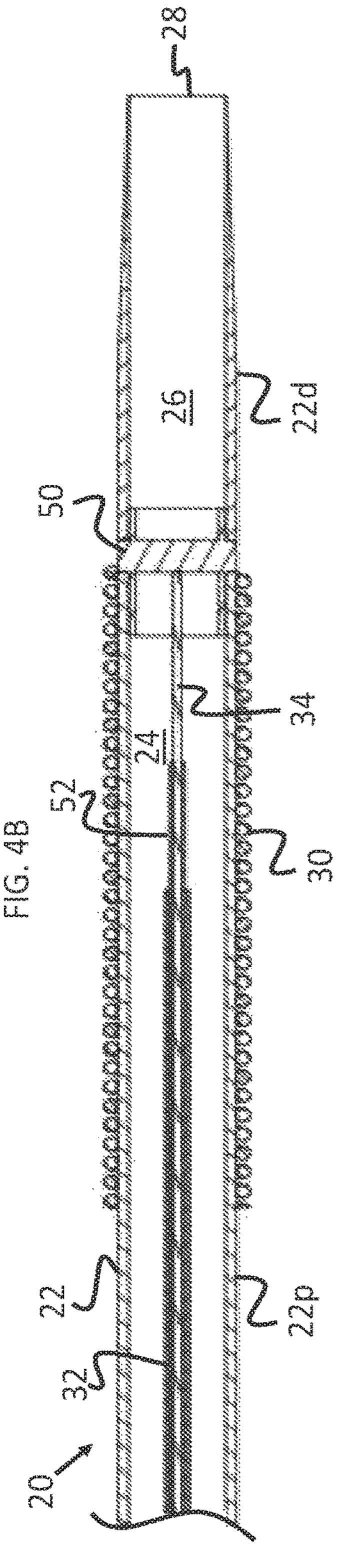
FIG. 4B is a schematic illustration of a longitudinal cross-section through the apparatus shown in FIG. 4A.

Reference is now made to FIG. 4A, which is a schematic illustration of apparatus 20, in accordance with other embodiments of the present invention. Reference is additionally made to FIG. 4B, which is a schematic illustration of a longitudinal cross-section through apparatus 20 as shown in FIG. 4A.

In some embodiments, second lumen 26 is distal to first lumen 24, e.g., such that the first lumen, but not the second lumen, has a proximal opening at the proximal end of the tube. Thus, advantageously, the diameter of each of the lumens may be greater than would otherwise be possible.

For example, tube 22 may comprise a proximal tube-portion 22*p* shaped to define the first lumen, and a distal tube-portion 22*d* connected distally to proximal tube-portion 22*p* and shaped to define the second lumen. A connector 50, comprising, for example, a cylindrical stopper, may seal the distal end of the proximal tube-portion and connect the proximal tube-portion to distal tube-portion 22*d*. In such embodiments, typically, outer electrode 30 is wrapped around the distal end of the proximal tube-portion.

As described above with reference to FIG. 1, the tube is passed through the blockage such that the outer electrode lies within the blockage, and a voltage is then applied between the electrodes. (Although not shown in FIG. 4B, proximal tube-portion 22*p* is typically shaped to define apertures 44.) In some embodiments, distal tube-portion 22*d* is tapered, such that the distal tube-portion may pass through the blockage more easily. For example, the distal tube-portion may comprise a cone-shaped distal tip.

Prior to applying the voltage, while applying the voltage, and/or subsequently to applying the voltage, at least one item may be passed through distal opening 28, as described above with reference to FIG. 1. In some embodiments, to facilitate the passage of a guidewire through distal tube-portion 22*d*, the distal tube-portion is shaped to define lateral access port 48.

In some embodiments, proximal tube-portion 22*p* is further shaped to define at east one other lumen having another distal opening.

As described above with reference to FIG. 1, first wire 34 connects the outer electrode to the power source. For example, connector 50 may be electrically-conductive and in contact with the outer electrode, and the first wire may be distally connected to the connector. (In general, connector 50 may be made of any of the materials from which end cap 40 (FIG. 1) is made.) As further described above with reference to FIG. 1, the first wire is typically covered by insulating layer 52 over the majority of its length.

Alternatively to comprising two tube-portions connected to one another, tube 22 may comprise an internal wall separating a proximal portion of the tube, which is shaped to define the first lumen, from a distal portion of the tube, which is shaped to define the second lumen. In such embodiments, the internal wall may function similarly to connector 50, the proximal portion of the tube may function similarly to proximal tube-portion 22*p*, and the distal portion of the tube may function similarly to distal tube-portion 22*d*.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a blockage in a body of a subject, the apparatus comprising:

a tube configured for insertion into the body and shaped to define:

a first lumen, and a second lumen having a distal opening; and a pair of electrodes comprising:

an outer electrode wrapped around the tube; and an inner electrode configured to pass through the first lumen;

wherein the tube has a wall comprising one or more apertures, the one or more apertures positioned beneath the outer electrode, and the pair of electrodes are configured such that upon application of voltage between the electrodes, an electric field is established through the one or more apertures between the inner electrode and the outer electrode;

wherein the inner electrode is in a fixed position relative to the tube, and wherein the tube and the pair of electrodes are configured such that, upon application of the voltage, an electric field is established in a radial direction with respect to a longitudinal axis of the tube.

2. The apparatus according to claim 1, wherein the tube is further shaped to define at least one other lumen having another distal opening.

3. The apparatus according to claim 1, wherein the first lumen and the second lumen are not in fluid communication with one another within the tube.

4. The apparatus according to claim 1, wherein the tube is shaped to define a lateral access port into the second lumen.

5. The apparatus according to claim 4, wherein the lateral access port is slit-shaped.

6. The apparatus according to claim 1, wherein the first lumen is distally closed.

7. The apparatus according to claim 6, wherein the inner electrode is axially moveable within the tube.

8. The apparatus according to claim 1, wherein the first lumen and the second lumen run alongside one another.

9. The apparatus according to claim 8, wherein the tube comprises an internal tubular divider separating the first lumen from the second lumen.

10. The apparatus according to claim 9, wherein the tubular divider comprises an inwardly-protruding portion of a wall of the tube.

11. The apparatus according to claim 8, further comprising:

an electrically-conductive cap that seals a distal end of the first lumen and contacts the outer electrode; and a wire passing through the first lumen and distally connected to the cap, such that the wire is configured to connect the outer electrode, via the cap, to a power source configured to apply the voltage.

12. The apparatus according to claim 11, wherein the wire passes through the inner electrode.

13. The apparatus according to claim 11, wherein the cap covers a distal tube-end of the tube and is shaped to define an aperture aligned with the distal opening.

14. The apparatus according to claim 1, wherein the second lumen is distal to the first lumen.

15. The apparatus according to claim 14, wherein the tube comprises an internal wall separating a proximal portion of the tube, which is shaped to define the first lumen, from a distal portion of the tube, which is shaped to define the second lumen.

16. The apparatus according to claim 14, wherein the tube comprises:

a proximal tube-portion shaped to define the first lumen; and a distal tube-portion connected distally to the proximal tube-portion and shaped to define the second lumen.

17. The apparatus according to claim 16, wherein the outer electrode is wrapped around the proximal tube-portion.

18. The apparatus according to claim 16, wherein the distal tube-portion is tapered.

19. The apparatus according to claim 16, wherein the proximal tube-portion is further shaped to define at least one other lumen having another distal opening.

20. The apparatus according to claim 1, wherein the first lumen is distally closed and wherein the tube is shaped to define the one or more apertures between the outer electrode and the inner electrode.

21. The apparatus according to claim 1, wherein the outer electrode is wrapped around a portion of the lumen through which at least a portion of the inner electrode is configured to pass.

22. The apparatus according to claim 1, wherein a distal portion of the tube has a tapered shape.

23. The apparatus according to claim 1, wherein the outer electrode defines one or more circumferential openings.

24. The apparatus according to claim 23, wherein at least one of the circumferential openings of the outer electrode is aligned with at least one of the apertures to allow at least a portion of the blockage to enter the tube.

25. The apparatus according to claim 24, comprising a suction-applying device configured to apply a suction force to the blockage via the one of the apertures.

26. A method for treating a blockage in a body of a subject, the method comprising:

inserting a tube into the body, the tube being shaped to define:

a first lumen, and a second lumen having a distal opening;

subsequently to inserting the tube, applying an electric current to the blockage, by applying a voltage between an outer electrode wrapped around the tube and an inner electrode passing through the first lumen;

wherein the tube has a wall comprising one or more apertures, the one or more apertures positioned beneath the outer electrode, and the inner electrode and the outer electrode are configured such that upon application of voltage between the electrodes, an electric field is established through the one or more apertures between the inner electrode and the outer electrode; and passing at least one item through the distal opening.

27. The method of claim 26, wherein the passing comprises passing the at least one item, either from or into the second lumen, and wherein the at least one item comprises one or more of: a guidewire, a contrast agent, a tool and a stent.

* * * * *